(12) United States Patent
Sweeney

(10) Patent No.: US 10,779,906 B2
(45) Date of Patent: Sep. 22, 2020

(54) CLEANING DEVICE WITH MICROFIBER TAILS

(71) Applicant: Shaun Sweeney, Wayne, NJ (US)

(72) Inventor: Shaun Sweeney, Wayne, NJ (US)

(73) Assignee: Cygnus Medical, LLC, Branford, CT (US)

( * ) Notice: Subject to any disclaimer, the term of this patent is extended or adjusted under 35 U.S.C. 154(b) by 518 days.

(21) Appl. No.: 15/209,281

(22) Filed: Jul. 13, 2016

(65) Prior Publication Data

US 2018/0014907 A1 Jan. 18, 2018

(51) Int. Cl.
*B08B 1/00* (2006.01)
*A61B 90/70* (2016.01)

(52) U.S. Cl.
CPC ........ *A61B 90/70* (2016.02); *A61B 2090/701* (2016.02)

(58) Field of Classification Search
USPC ............... 15/104.16, 104.165, 104.17, 104.5
See application file for complete search history.

(56) References Cited

U.S. PATENT DOCUMENTS

| | | | | |
|---|---|---|---|---|
| 2,790,987 A * | 5/1957 | Kirkpatrick | .............. | A46B 3/18 15/206 |
| 3,582,140 A * | 6/1971 | Kaufman | .................. | A46B 3/18 15/206 |
| 4,215,478 A * | 8/1980 | Thomas | .................. | A61C 15/02 132/323 |
| 5,168,593 A | 12/1992 | Poje et al. | | |
| 5,297,310 A | 3/1994 | Cox et al. | | |
| 6,699,331 B1 | 3/2004 | Kritzler | | |
| 7,097,629 B2 | 8/2006 | Blair | | |
| 8,065,772 B2 | 11/2011 | Maguire, Jr. et al. | | |
| 8,177,553 B2 * | 5/2012 | Stoll | ........................ | A61C 5/85 132/329 |
| 8,479,344 B2 | 7/2013 | Maslanka | | |
| 8,651,116 B2 * | 2/2014 | Slack | ................... | A61C 15/041 132/200 |
| 9,296,024 B2 * | 3/2016 | Sweeney | ................. | B08B 9/043 |
| 2001/0016962 A1 | 8/2001 | Moore et al. | | |
| 2003/0040733 A1 | 2/2003 | Cragg et al. | | |
| 2004/0187892 A1 * | 9/2004 | Maguire, Jr. | ............ | A46B 3/18 134/8 |

(Continued)

FOREIGN PATENT DOCUMENTS

DE 102010026774 A1 1/2012
EP 2712533 A2 4/2014

*Primary Examiner* — Joseph J Hail
*Assistant Examiner* — Shantese L McDonald
(74) *Attorney, Agent, or Firm* — St Onge Steward Johnston & Reens LLC

(57) ABSTRACT

A cleaning device for lumens includes a plurality of microfiber tails and a flexible leader. The microfiber tails are elongated, flat tails having substantially the same length and width. At two ends of the tails, the width of the tails tapers to form a cone shape. The microfiber tails are oriented in planar parallel relationship to one another or layered on top of one another when laid on a flat surface. The flexible leader has a first end and a second end, the second end of the flexible leader is adapted to be fed through the lumen and pulled by the first end thereof through the lumen, with the microfiber tails also being adapted to be pulled through the lumen due to its being coupled to the second end of the flexible leader.

21 Claims, 4 Drawing Sheets

(56) References Cited

U.S. PATENT DOCUMENTS

| | | |
|---|---|---|
| 2004/0187893 A1 | 9/2004 | Maguire, Jr. et al. |
| 2006/0049386 A1 | 3/2006 | Kody et al. |
| 2006/0102200 A1 | 5/2006 | Esquenet et al. |
| 2006/0191087 A1* | 8/2006 | Maguire, Jr. ............ A46B 3/18 15/104.16 |
| 2009/0113644 A1 | 5/2009 | Heck |
| 2009/0276971 A1 | 11/2009 | Nozari |
| 2010/0145143 A1 | 6/2010 | Salomon et al. |
| 2010/0229318 A1 | 9/2010 | Sparks |
| 2011/0289705 A1 | 12/2011 | Asano et al. |
| 2012/0198639 A1* | 8/2012 | Smith ..................... A46B 3/18 15/104.05 |
| 2012/0324661 A1 | 12/2012 | DeDominicis et al. |
| 2013/0269134 A1 | 10/2013 | Lin |
| 2014/0215736 A1 | 8/2014 | Gomez et al. |
| 2014/0228677 A1 | 8/2014 | Grudem, Jr. et al. |
| 2014/0250614 A1 | 9/2014 | Pisacane |
| 2015/0059206 A1* | 3/2015 | Lovett .................. A43C 11/165 36/50.1 |

* cited by examiner

CLEANING DEVICE WITH MICROFIBER TAILS

FIELD OF THE INVENTION

The present invention relates to cleaning devices for cleaning lumens. More specifically, the invention relates to flexible cleaning devices for use in connection with cleaning endoscopes and other instruments having lumens or other similar configurations.

BACKGROUND OF THE INVENTION

Surgical instruments, such as flexible and nonflexible endoscopes, surgical lumens, and other medical paraphernalia used in healthcare facilities must be cleaned and sterilized before every procedure. This cleaning typically takes place as a preliminary step subsequent to use and soiling of the surgical instruments, and prior to their sterilization.

However, the physical designs of most models of endoscopes make the cleaning of every internal surface difficult. It has been a common practice to merely soak used surgical instruments such as biopsy channels or lumens in a detergent bath and scrubbing with a small scrub brush prior to their being sterilized. Since delicate material is often used to make flexible endoscopes, scrub brushes longer than about 2.0 cm have a tendency to damage the lumen. Moreover, small scrub brushes cannot thoroughly scrub the internal surfaces of surgical lumens resulting in contaminants remaining throughout surgical lumens. Pushing a conventional scrub brush through a lumen is also problematic because it may damage the lumen wall.

The problem of surgical instrument cleaning is further compounded by biological residue left on the surgical instruments from the patient's body after each surgical operation. This residue must be completely removed prior to sterilization. Some of these biological residues can be resilient and difficult to remove from the instruments. For example, opportunistic organisms such as bacteria and fungi from the ambient environment and/or patient may colonize the instruments and produce a crude extra-cellular matrix in order to protect the cells in their colonies. This matrix is referred to as biofilm and usually comprises a disorganized web of long polymer strands interspersed with live cells and proteins. Biofilm is a highly effective anchoring and protection for bacterial and fungal colonies—as a result it is notoriously difficult to clean. Once a medical instrument is coated in biofilm, it is very difficult to fully clean and sterilize. Therefore, vigorous cleaning throughout the entire instruments, such as through the entire length of a surgical lumen, both inside and out, is required. But the lumen interior is not physically accessible for vigorous scrubbing compared to an exterior surface of a medical instrument.

The state of the art for cleaning and removing biofilm from lumen interiors is essentially limited to detergent delivery systems (i.e., suctioning detergent through the lumen) and basic scrubbing devices. Many lumen cleaners use a "push through" design whereby a short scrubber is pushed through the lumen. A short scrubber is used to prevent buckling as the scrubber moves through the channel.

Cygnus Medical, LLC developed a pull-through design channel brush suitable for endoscopic channel cleaning. The Caterpillar™ brush uses a relatively rigid leader that is threaded through a channel to pull a relatively long brush, about 12 inches, through the channel for improved cleaning. The brush is in the form radially extending bristles secured in the twisted wire core in a helical or spiral manner. Although the Caterpillar™ represents a significant improvement over conventional scrubbing devices for lumens, it employs a conventional scrubber brush and its ability to remove biofilm could be improved.

Cygnus Medical, LLC discloses another type of channel brush in U.S. Pat. No. 9,296,024. The channel brush comprises a pulling device and a scrubber in the form of braided or twisted cleaning threads, wherein each cleaning thread is composed of a microfiber strand braided with a foam strand.

There remains a need in the art for a medical instrument cleaning device that can effectively and efficiently abrade, dislodge, and remove biofilm or any other contaminations from the interior of a catheter or endoscope lumen. Preferably, the cleaning device is simple and straightforward enough to be utilized by personnel requiring a minimum amount of training.

SUMMARY OF THE INVENTION

It is an object of the present invention to provide a cleaning device which is durable and flexible.

It is another object of the present invention to provide a cleaning device that provides a simple and cost efficient mechanism for cleaning lumens by providing direct access to the internal surfaces of lumens.

It is a further object of the present invention to provide a cleaning device that increases the effectiveness and reliability of pre-sterilization cleaning.

It is yet another object of the present invention to provide a cleaning device that removes and dissolves blood, fat, proteins, mucous and other organic contaminates from soiled surgical lumens.

It is a further object of the present invention to provide a cleaning device that does not damage a lumen wall.

It is a further object of the present invention to provide a cleaning device that decreases the probability that a cleaning portion thereof will unintentionally become detached from a leader portion thereof.

These and other objects of the present invention are achieved, in accordance with one embodiment of the present invention, by provision of a cleaning device for lumens such as lumens of surgical instruments. The cleaning device comprises a flexible leader having a first end and a second end, a plurality of individual elongated tails connected to the leader at its second end. The leader is adapted to be threaded through the lumen of the surgical instruments and pulled by the first end thereof through the lumen, with the plurality of individual tails also being adapted to be threaded through the lumen due to its being coupled to the second end of the leader.

In some embodiments, each of the tails has a flat, hourglass shape, which may be folded at a midpoint to form a loop, wherein the loop is coupled to the second end of the leader. In other embodiments, the tails are connected to each other at at least one location, and the connected tails are further coupled to a leader. In further embodiments, each of the tails are directly coupled to the leader by any known techniques using a variety of materials. The plurality of individual tails coupled to the leader may be oriented in planar parallel arrangement with respect to one another (side-by-side in a width-wise direction). Alternatively, they may be in parallel arrangement length-wise, yet some of the tails are partially overlay or completely overlay (i.e., stack) on each other.

In some embodiments, each tail has a width of about 1 mm to about 10 mm. In preferred embodiments, the width of each tail tapers to form a cone shape at both ends of the tail. In some embodiments, the length of each tail is about 8 inches (or about 200 mm). The cleaning device may have one to six, preferably, three to five, more preferably, two to four microfiber tails.

The leader of the cleaning device should be made of material with a reasonable rigidity or stiffness sufficient to pass it through a soiled lumen. The leader is preferably long enough to pass all the way through the entire lumen.

A joint is formed where the second end of the leader is coupled to the tails. In some embodiments, the cleaning device further comprises a jacket to cover the joint. The jacket has a smooth surface, which helps to reduce the likelihood of damage to the lumen of the surgical instrument during cleaning thereof. It also secures the coupling between the leader and the microfiber tails, and prevents them from being pulling apart during use. The jacket may be made of a polymer material, such as nylon.

In accordance with another aspect of the present invention, a method for forming a cleaning device for lumen of surgical instruments comprises the steps of laser cutting a microfiber fabric into a plurality of individual tails of substantially same shape, folding each of the tails at the middle point to form a loop, and coupling the loop of each of the tails to a flexible leader.

Laser cutting provides consistent and precise cutting of microfiber fabric to afford tails of a uniform shape, it also ensures that the microfiber tails are lint-free. Because they are fiber free, the tails are less prone to wear and tear during use.

DETAILED DESCRIPTION OF THE INVENTION

Figure 1:
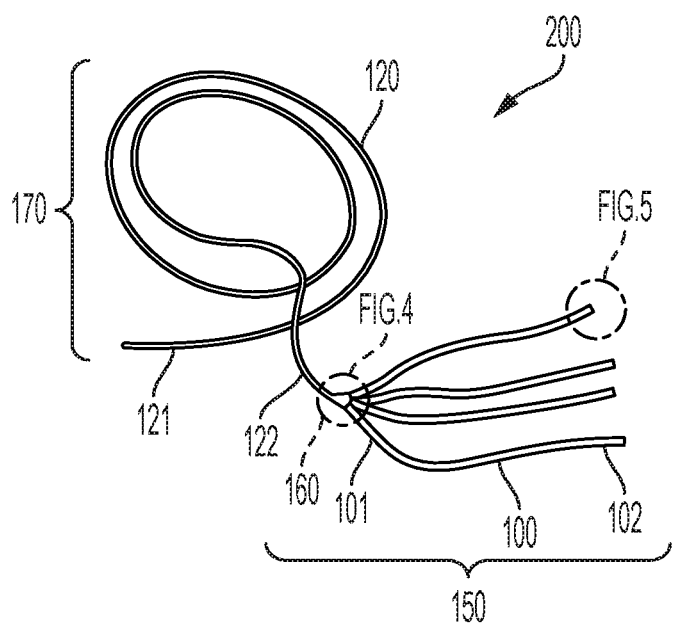
FIG. 1 is a schematic view of a cleaning device having a plurality of microfiber tails and a leader in accordance with one embodiment of the present invention.
Figure 2:
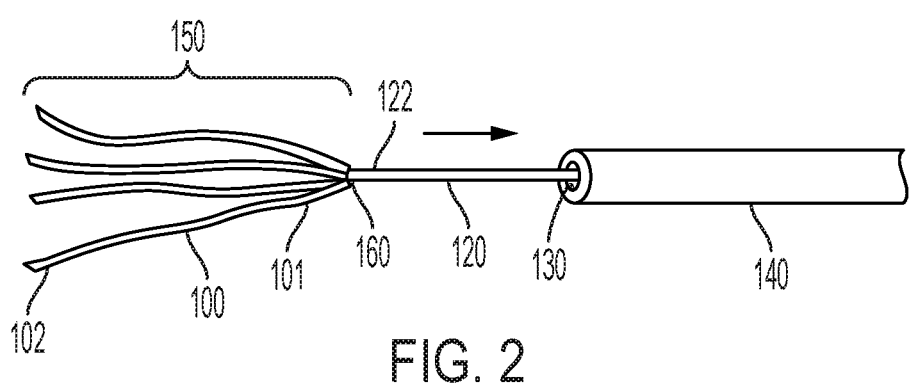
FIG. 2 is a schematic view of a cleaning device being pulled into an endoscopic lumen in accordance with one embodiment of the present invention.

Referring to FIG. 1, a cleaning device 200 according to the present invention comprises a leader portion 170 and a cleaning portion 150. Leader portion 170 includes a long and flexible leader 120 with a first end 121 and a second end 122. Leader 120 can also be called a pulling device. Cleaning portion 150 comprises a plurality of individual microfiber tails 100. Microfiber tails 100 are elongated, flat strands having substantially same dimensions. Microfiber tails 100 can also be called microfiber strands. Preferably, microfiber tails 100 are lint-free. Each tail 100 has a first end 101 and a second end 102. The second end 122 of leader 120 is coupled to the first end 101 of each tail 100 to form a joint 160. When in use, leader 120 is threaded through a lumen 130 of a surgical instrument 140, which pulls plurality of tails 100 through lumen 130 for cleaning the interior of lumen 130, as shown in FIG. 2.

Figure 9:
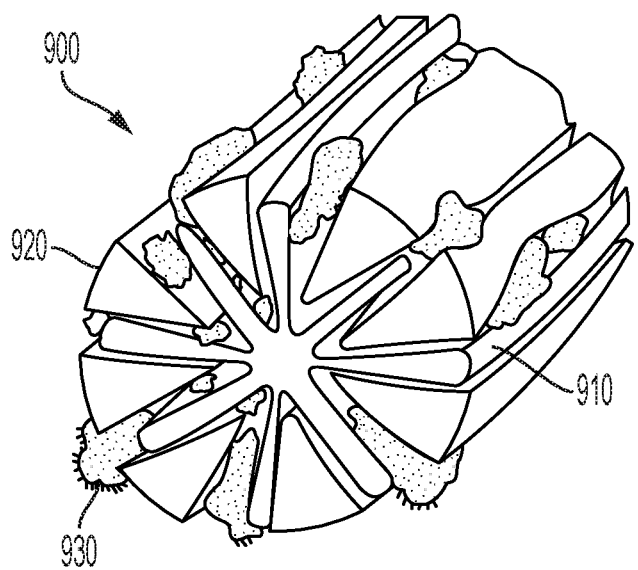
FIG. 9 is a microscopic view of microfiber accumulating particles of biofilm.

The microfiber tails 100 comprise microfiber fabric that has a microscopic structure allowing it to remove particles of biofilm adhered to a surface and to capture and retain the particles, thereby sweeping up them from the surface. As one skilled in the art would understand, microfiber fabric is made up a plurality of ultra-fine fibers (e.g., finer than one denier or less). FIG. 9 shows a microscopic view of an exemplary single fiber 900, e.g., a split microfiber, which may be used to create the microfiber fabric. In this embodiment, the microfiber 900 may have a star component 910 and several wedge components 920. When the microfiber 900 contacts biofilm particles 920, the particles 920 are pulled into the microfiber 900 and become trapped between the star component 910 and one of the wedge components 920. If sufficient microfiber fabric is used, substantially all of the particles may be dislodged and swept up by the microfiber fabric and completely removed from the instrument surface when the cleaning device is removed.

In addition to biofilm particles, other debris can be removed from the lumen 130 with the microfiber tails 100 once the microfiber tails 100 have been fully pulled through the lumen 130. Microfiber tails 100 are capable of capturing microscopic particles or debris as small as four microns. Microfiber tails 100 may be soaked in detergent or surfactant to aid the process by further chemically degrading the biofilm. Microfiber tails 100 may also be soaked in disinfectant to aid a decontamination process. In those cases, the microfiber tails 100 retain the detergent, surfactant, or disinfectant, and delivers it to the interior surface of the lumen 130.

Figure 3:
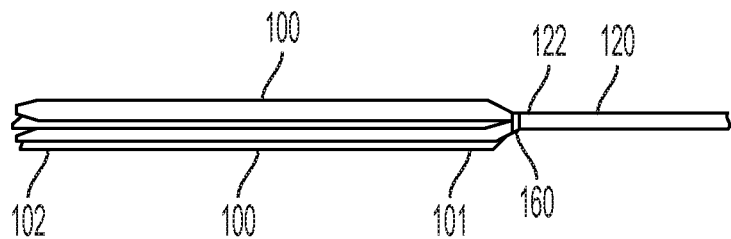
FIG. 3 is a close-up schematic view of a plurality of microfiber tails being laid on a flat surface in accordance with one embodiment of the present invention.

FIG. 3 is a close-up schematic view of a plurality of microfiber tails 100 when they are laid on a flat surface, according to one embodiment of the present invention. Each tail 100 has substantially the same length and width. Each tail 100 also has the same thickness. Each tail is typically as thin as a piece of a cloth. Tails 100 are coupled onto the leader 120 in such a way that the tails 100 are in planar parallel arrangement with respect to one another (side-by-side in a width-wise direction). In some embodiments, they may be in a parallel arrangement in a thickness direction, yet some of the tails are partially overlay or completely overlaid (i.e., stacked) on each other.

Figure 4:
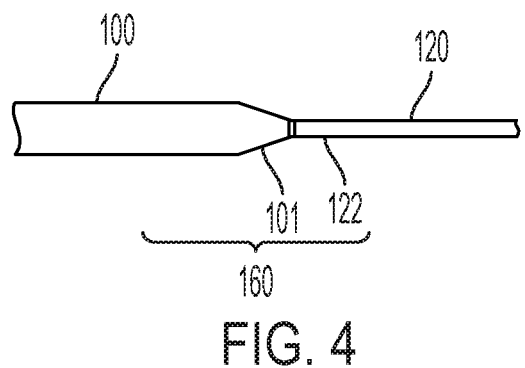
FIG. 4 is a close-up schematic view of a first end of a microfiber tail coupled with a leader in accordance with one embodiment of the present invention.
Figure 5:
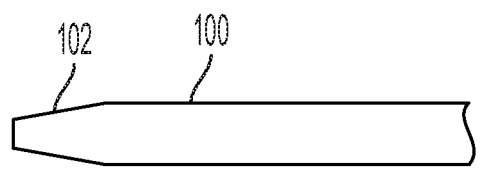
FIG. 5 is a close-up schematic view of a second end of a microfiber tail in accordance with one embodiment of the present invention.

FIGS. 4 and 5 present close-up views of first and second ends 101, 102 of tail 100, according to some embodiments of the present invention. The width of the tails 100 may be from about 1 mm to about 10 mm, and preferably about 2 mm to about 5 mm. The cleaning devices may be offered in many different sizes for different tube sizes, such as a first size for 2.0-2.4 mm tubes, a second size for 2.8-3.2 mm tubes, and a third size for 3.5-4.2 mm tubes. In each, the width of the tails is proportional to the tube size. At the first end 101 (closer to leader 120), the width of tail 100 is smaller which advantageously facilitates the coupling of tail 100 with leader 120 and prevents joint 160 from becoming too bulky. In some embodiments, as shown in FIG. 4, the tail 100 tapers to a certain degree towards its first end 101 to form a cone shaped piece. The width of tail 100 at second end 102 may be the same or smaller than the width of main part of tail 100. Preferably, tail 100 also tapers to a certain degree towards its second end 102 to form a cone shaped piece. Tapering at the distal end of the tails 100 advantageously prevents curling of the tails 100 as they end the lumen 130.

Further, Applicant found that by reducing the width of each tail at the end, the collective diameter of the tail ends is smaller than that of the main body of tails, thereby creating a bulging shape of tails inside a lumen wherein the middle part of tails has, collectively, the largest diameter. This configuration advantageously helps to keep a detergent retained longer in the lumen and also facilitate that the abrading and cleaning of the interior wall of the lumen by the tails. Each of the tail ends will have room to move and orientate itself inside the lumen, which causes an orientation change of the middle part of the tails (in other words, strands are not stuck onto the wall in fixed contact areas), thereby exposing more surfaces of the tails to be in contact with the interior walls of lumen.

The length, the width, and the number of the tails for the medical cleaning device may vary. They largely depend on the volume of channels to be cleaned. In some embodiments, the length of the tails is about 8 inches (or about 200 mm). The width of each tail times the number of tails on each medical cleaning device correlates to the diameter of the tails when they are bundled together. Generally, tails 100, when loosely bundled together, should have a diameter, in the middle part, approximately 10% to 20% larger than lumen 130 to ensure snug fit between tails 100 and lumen 130 as tails 100 is pulled through so that tails 100 can abrade and clean the interior wall of lumen 130. Channels in endoscopes typically have a diameter in the range of about 2.0 mm to about 4.5 mm. In some embodiments, medical cleaning devices with microfiber tails are specifically configured for cleaning channels of about 2.0 mm to about 2.4 mm in diameter. In other embodiments, cleaning devices with microfiber tails are specifically configured for cleaning channels of about 2.8 mm to about 4.2 mm in diameter. In yet other embodiments, cleaning devices with microfiber tails are specifically configured for cleaning channels of about 3.5 mm to about 3.7 mm in diameter. In some embodiments, the cleaning devices are employed for cleaning larger channels, such as gun barrels, having diameters of 5 mm and above.

While more tails will provide more surface areas for scrubbing and cleaning, too many tails may cause them to tangle more easily. Typically, the medical cleaning device have one to six, preferably, three to five, more preferably, two to four, and even more preferably, two tails of microfiber tails.

Microfiber tails are prepared by using a laser cutting technology. The laser cutting advantageously provides consistent and precise cutting of microfiber fabric which yields tails of uniform shapes. It also ensures that the microfiber tails do not tear or fray and are lint-free. Because they are lint-free, the tails are less prone to wear and tear during use. As such, the present invention provides a durable cleaning device.

Leader 120 may be made from any suitable resin, plastic, or thermoplastic elastomer, and combinations thereof. Preferably, leader 120 is made out of flexible polyvinyl chloride (PVC). The leader 120 may be made out of metal wire, or twisted wire segments. Leader 120 may be made out of a polymer thread similar to fishing wire. Leader 120 may be a hollow tube made of any of the above materials.

The leader 120 is made of material with a reasonable rigidity or stiffness sufficient to pass it through a soiled lumen. The desired stiffness may be achieved by utilizing a stiff polymer to form leader, e.g. PVC, or nylon, inserting a support wire (e.g., a conventional soft steel or iron wire) into a hollow tube of leader, or using a braided wire and polymer thread to form leader. When wire is used, the leader 120 is preferably coated with a polymer layer or jacket (e.g., heat shrink tubing), preferably made of nylon.

Referring back to FIG. 2, the leader 120 is preferably long enough to be passed all the way through the lumen 130 so that a user can pass the first end 121 all of the way through the inside of the lumen 130 so that the first end 121 extends out of the lumen 130 opposite the receiving end of the lumen, while the second end 122 remains below the receiving end of the lumen 130. The leader 120 is preferably cylindrical in shape, having a predetermined, and generally consistent, diameter. Any diameter of the leader 120 may be utilized as long as it is smaller than the diameter of the lumen 130 so that the leader 120 can flexibly pass through the inside of the lumen 130 without damaging the lumen walls. In some embodiments, leader 120 has a diameter of from about 0.5 mm to about 4.0 mm, preferably about 1.5 mm to about 2.7 mm.

Referring back to FIG. 1, the second end 122 of the leader 120 is attached to the first end 101 of each tail 100 to form the joint 160. Joint 160 may be made by any known techniques using a variety of materials. For example, the first end 101 of each tail 100 may be tied onto the second end 122 of the leader 120 using a separate piece, such as a tie, a string, or a wrap. Alternatively, the first end 101 of each tail 100 may be wrapped around the second end 122 of the leader 120 so that the two pieces are tied together. Moreover, the first end 101 of each tail 100 and the second end 122 of the leader 120 may be bonded by utilizing a heat shrink wrap, a bonding resin, or adhesive cement.

Figure 6:
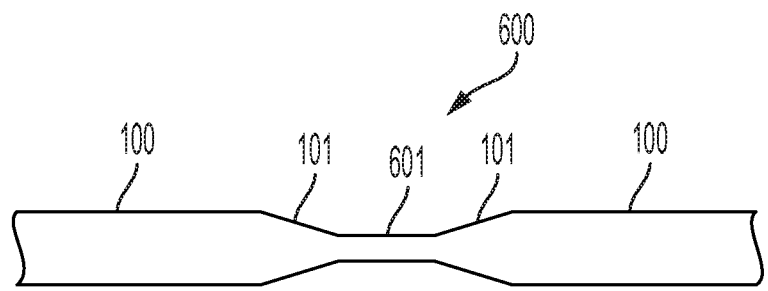
FIG. 6 is a close-up schematic view of a portion of an hourglass shape tail in according with one embodiment of the present invention.
Figure 7:
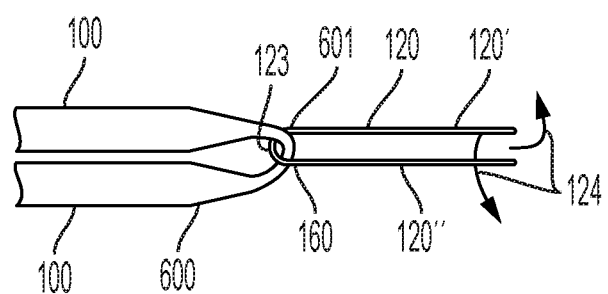
FIG. 7 is a schematic view showing a method for joining a leader and microfiber tails in accordance with one embodiment of the present invention.

FIGS. 6 and 7 show joining of the leader 120 and the microfiber tails 100 in accordance with one embodiment of the present invention. The microfiber fabric is laser cut to form pieces or strands, each piece or strand having an hourglass shape 600, as shown in FIG. 6. The midpoint 601 of the hourglass shaped piece 600 has the smallest width. The piece 600 may be folded along the midpoint 601 to form two tails 100, as shown in FIG. 7. In FIG. 7, the leader 120 is in the form of a twisted metal wire, twisted polymeric thread, or combination thereof, which is made by first forming a pair of segments 120',120" connected at one end 123, also called a folding point 123, to form a substantially "U" shape. Preferably, the leader 120 is a metal wire, which may be of a type that is well known in the art, e.g., a conventional soft steel or iron wire, the dimensions and specifications of which are also well known. Segments 120',120" may each be a metal wire or twisted wire core in a helical or spiral manner. The hourglass shape piece 600 is placed between segments 120', 120" by straddling two tails 100 on segments 120',120" at the folding point 123 (which happens to be 160 and could also be the midpoint 601). In other words, the hourglass shape piece 600 loops around the leader 120 at the folding point 123. Segments 120',120" are then twisted (see arrows 124 in FIG. 7) to secure the joint 160 at the folding point 123. As a result, two tails are formed from each hourglass shape piece 600. The device therefore has an even number of tails.

Although FIG. 7 shows that only one piece 600 is joined to leader 120, one skilled in the art would understand that other pieces 600 may be joined to the leader 120 in the same or similar manner to form additional tails 100.

Figure 8:
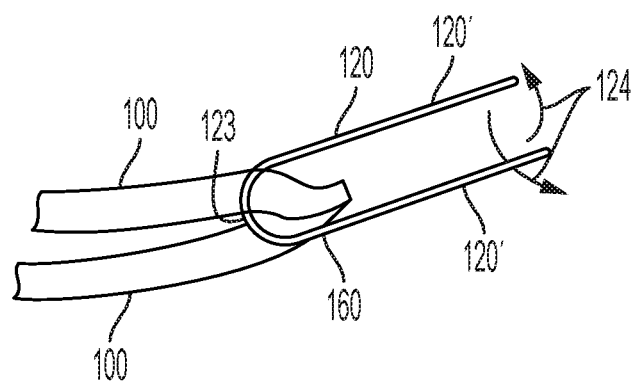
FIG. 8 a schematic view showing another method for joining a leader and microfiber tails in accordance with another embodiment of the present invention.

FIG. 8 illustrates another method of joining the leader 120 and microfiber tails 100 in accordance with another embodiment of the present invention. Two or more tails 100 are first bonded together at their first ends 101 an adhesive, thermal bonding, sonic welding, or another type of bonding method. For a simple illustration, FIG. 8 shows the two tails 100 bonded together. Leader 120 in the form of a twisted metal wire, twisted polymeric thread, or combination thereof, which is made by first forming a pair of segments 120',120" connected at one end 123, also called the folding point 123, to form a substantially "U" shape. Bonded tails 100 are placed between the segments 120',120" by straddling the two tails 100 on the leader 120 at the folding point 123 (which also happens to be 160). Segments 120',120" are then twisted (see arrows 124 in FIG. 8) to secure joint 160 at folding point 123.

Figure 10:
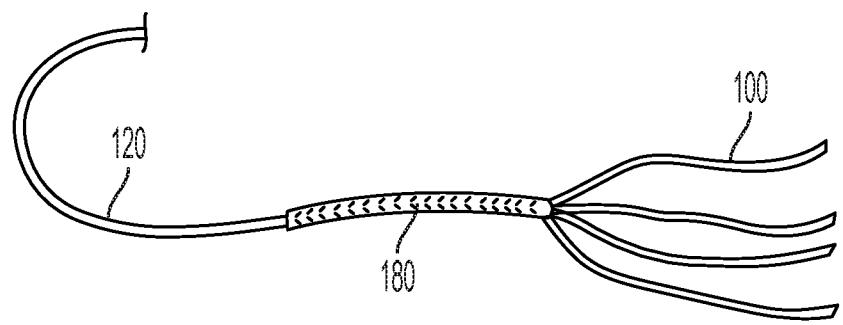
FIG. 10 is a schematic view of a cleaning device having a plurality of microfiber tails, a leader, and a jacket covering area where the tails and the leader are connected, in accordance with one embodiment of the present invention.

While it is possible to form the joint 160 having a smooth outer surface, thereby reducing the likelihood of damage to the lumen of the surgical instrument during cleaning thereof, in some embodiments, as shown in FIG. 10, a jacket 180 (e.g., heat shrink tubing) may be provided over a portion of the leader 120 and a portion of the tails 100 near the joint 160. The jacket 180 provides a smooth outer surface, which is in contact with contacts the lumen of the surgical instrument during cleaning thereof. The jacket 180 secures the coupling between the leader 120 and the microfiber tails 100, and prevents the microfiber tails 100 from being torn or slipping off the leader 120 during use. Jacket 180 may be formed from any of numerous materials, although it has been found that polymer materials, particularly nylon, provide desirable results.

A comparative study shows that the cleaning devices with microfiber tails are more efficient and effective in cleaning contaminations, compared to a traditional style channel brush.

Inoculated Sample Preparation:

An artificial test soil was used to inoculate seven channels for testing. The test artificial test soil mimicked the worst case contaminants (blood and proteins) that may come in contact with a medical device, and remain on the device after clinical use.

Cleaning Procedures:

Three inoculated channels were cleaned with a traditional style channel brush with bristles. In each cleaning, one channel brush and one inoculated channel were submerged in sterile water. The brush was pulled through one time, under sterile water without the use of detergents or rinsing. This test was repeated twice using a different inoculated channel with a fresh channel brush each time.

Three other inoculated channels were cleaned with the medical cleaning device with microfiber tails of the present invention. In each cleaning, one medical cleaning device with microfiber tails and one inoculated channel were submerged in sterile water. The medical cleaning device was pulled through one time, under sterile water without the use of detergents or rinsing. This test was repeated twice using a different inoculated channel with a fresh medical cleaning device each time.

One inoculated channel was intentionally left uncleaned. The uncleaned, inoculated channel was used as a positive control in the study.

Test Results:

The residual protein in each of the six channels after cleaning and the protein in the positive control channel were measured and recorded. % Reduction and log reduction were calculated (Tables 1 and 2, respectively) to compare the effectiveness of cleanings by use of the two different channel cleaning devices.

TABLE 1

Residual Protein in the Cleaning Channel (μg = micrograms)

| SAMPLE ID | | TEST SAMPLES | NEGATIVE CONTROL |
|---|---|---|---|
| Residual protein in the cleaning channel after using the Dragontail Channel Brush. | Channel 1 | 56 μg | Less than 10 μg |
| | Channel 2 | 70 μg | |
| | Channel 3 | Less than 10 μg | |
| Residual protein in the cleaning channel after using a Competitor's Channel Brush. | Channel 1 | 23,475 μg | Less then 10 μg |
| | Channel 2 | 14,398 μg | |
| | Channel 3 | 21,121 μg | |
| Cleaning channel Positive Control. | | 295,649,037 μg Protein embedded in FDA test soil. | |

TABLE 2

Residual Protein in the Cleaning Channel - % Reduction and Log Reduction

| SAMPLE ID | | % REDUCTION | LOG REDUCTION |
|---|---|---|---|
| Residual protein in the cleaning channel after using the Dragontail Channel Brush. | Channel 1 | 99.98% | 3.8 |
| | Channel 2 | 99.97% | 3.7 |
| | Channel 3 | 99.99% | 4.5 |
| Average | | 99.98% | 4.0 |
| Residual protein in the cleaning channel after using a Competitor's Channel Brush. | Channel 1 | 92.06% | 1.1 |
| | Channel 2 | 95.13% | 1.3 |
| | Channel 3 | 92.86% | 1.2 |
| Average | | 93.35% | 1.2 |

The above results illustrate that the cleaning devices with microfiber tails are superior to the traditional style channel brush in terms of contamination reduction. The cleaning devices with microfiber tails were able to reduce contamination by 4 log with one pass under the above described condition, while the traditional style channel brush can only reduce contamination by 1.2 log under the same condition.

It should also be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A cleaning device for a lumen, comprising:
   a flexible leader having a first end and a second end;
   a plurality of elongated flat microfiber strands, each strand having a midpoint with a portion of reduced width, each strand being folded at the midpoint to form a loop coupled to the second end of the leader and two tails of same length thereby forming an even number of tails, wherein the strands are attached to one another at the midpoints and detached from one another at the tails;
   wherein the leader is adapted to be threaded through the lumen and pulled by the first end thereof through the lumen, with the plurality of elongated strands also being adapted to be threaded through the lumen due to its being coupled to the second end of the leader; and wherein the plurality of elongated strands extends distally from the second end of the leader.

2. The cleaning device of claim 1,
wherein the leader comprises a pair of metal wire segments connected to each other at a folding point,
wherein the loop of each strand is coupled with the leader by straddling on the two wire metal segments at the folding point, and
wherein the twisting of the pair of the two metal wire segments secures the tail at the folding point.

3. The cleaning device of claim 1, wherein the plurality of individual tails are oriented in planar parallel relationship to one another or in parallel arrangement with the tails partially overlaying or completely overlaying on top of one another.

4. The cleaning device of claim 1, wherein each tail has a width of about 3.0 mm to about 10.0 mm.

5. The cleaning device of claim 1, wherein at a distal end of each tail, the width of each tail tapers to form a cone shape.

6. The cleaning device of claim 1, comprising two to six of the tails.

7. The cleaning device of claim 6, comprising two to four of the tails.

8. The cleaning device of claim 1, further comprising a jacket covering a portion of the leader and a portion of each of the strands in an area where the leader couples with the plurality of the elongated strands.

9. The cleaning device of claim 8, wherein the jacket is made of a heat shrink polymer material.

10. The cleaning device of claim 1, wherein each of the plurality of elongated strands has a length that is greater than an inner diameter of the lumen.

11. A cleaning device for lumen, comprising:
a plurality of individual flat elongated microfiber tails each having a same length and width, each individual tail having a proximal end and a distal end,
wherein the plurality of individual tails are oriented in parallel arrangement with respect to one another; and
wherein the proximal end of each tail is coupled with a pulling device such that the tails are attached to one another at the proximal ends and detached from one another at the distal ends;
wherein a width of each of the tails tapers at each of the proximal and distal ends.

12. The cleaning device of claim 11, wherein each individual tail has a width of about 3.0 mm to about 10.0 mm.

13. The cleaning device of claim 12, wherein the pulling device comprises stainless steel braided wire.

14. The cleaning device of claim 12, wherein each tail is about 8 inches in length.

15. The cleaning device of claim 11, comprising four to six microfiber tails.

16. The cleaning device of claim 11, further comprising a jacket covering a portion of the pulling device and a portion of each of the microfiber tails in an area where the pulling device couples with the plurality of microfiber tails.

17. The cleaning device of claim 16, wherein the jacket is made of a polymer material.

18. A method for preparing a cleaning device, comprising steps of:
laser cutting a microfiber fabric into a plurality of individual flat microfiber strands having a same shape, wherein each individual strand has an hourglass shape at a middle point;
folding each of the strands at the middle point to form a loop with two tails; and
coupling the loop of each of the strands to a flexible leader such that the strands are attached to one another at the loops and detached from one another at the tails;
wherein the plurality of elongated strands extends distally from the second end of the leader.

19. The method of claim 18,
wherein the flexible leader comprises a metal wire,
wherein the coupling step comprises:
folding the metal wire of the leader into a pair of metal wire segments at a folding point;
straddling the loop of each strand on the metal wire segments at the folding point;
twisting the pair of metal wire segments at the folding point to form twisted wires and to secure coupling of the loop and the metal leader.

20. The method of claim 18, further comprising:
providing a jacket to cover a portion of the leader and a portion of each of the strands in an area where the loop and the metal leader are coupled to each other and an adjacent area thereof;
wherein the jacket is formed from nylon.

21. The method of claim 18, wherein each of the tails has a distal end with a tapering width.

\* \* \* \* \*